United States Patent [19]

Liu et al.

[11] Patent Number: 5,494,620
[45] Date of Patent: Feb. 27, 1996

[54] METHOD OF MANUFACTURING A MONOFILAMENT SUTURE

[75] Inventors: Cheng-Kung Liu, Norwalk; Richard P. Stevenson, Colchester, both of Conn.

[73] Assignee: United States Surgical Corporation, Norwalk, Conn.

[21] Appl. No.: 158,098

[22] Filed: Nov. 24, 1993

[51] Int. Cl.$^6$ ............................ D01D 5/088; D01D 5/12; D01D 10/02
[52] U.S. Cl. .................. 264/28; 264/210.8; 264/211.14; 264/235.6
[58] Field of Search .................................. 264/28, 210.8, 264/211.12, 211.14, 235.6, 237, 346

[56] References Cited

U.S. PATENT DOCUMENTS

| | | |
|---|---|---|
| 2,328,125 | 8/1943 | Buchsbaum et al. ............... 264/28 X |
| 3,054,652 | 9/1962 | Heumann . |
| 3,092,891 | 6/1963 | Baratti . |
| 3,106,442 | 10/1963 | Compostella et al. . |
| 3,112,508 | 12/1963 | Munt . |
| 3,449,476 | 6/1969 | Furness et al. ....................... 264/28 |
| 3,630,205 | 12/1971 | Listner . |
| 4,415,522 | 11/1983 | Capaccio . |
| 4,583,266 | 4/1986 | Tango et al. . |
| 4,806,737 | 2/1989 | Coates . |
| 4,808,358 | 2/1989 | Beretta . |
| 4,832,025 | 5/1989 | Coates . |
| 4,909,976 | 3/1990 | Cuculo et al. . |
| 4,911,165 | 3/1990 | Lennard et al. . |
| 4,970,038 | 11/1990 | Stanko . |
| 5,217,485 | 6/1993 | Liu et al. . |
| 5,227,110 | 7/1993 | Fischer et al. . |
| 5,236,444 | 8/1993 | Muth et al. . |

FOREIGN PATENT DOCUMENTS

| | | |
|---|---|---|
| 0415783 | 8/1990 | European Pat. Off. . |
| 1588031 | 7/1977 | United Kingdom . |

OTHER PUBLICATIONS

J. Gordon Cook, "Handbook of Polyolefin Fibers"; 1967; Merrow Publishing Co. Ltd., England; p. 52.
Abstract of JP-B-47 006 051 (Asahi Chemical Ind. Co. Ltd. from Database WPI Section Ch., Week 7208, Derwent Publications Ltd., London GB(published Jan. 28, 1969).
Search Report from the European Patent Office (EPO Search Report)(Mar. 9, 1995).

*Primary Examiner*—Leo B. Tentoni

[57] ABSTRACT

A process and apparatus are provided for manufacturing monofilaments possessing improved physical characteristics such as knot-pull and straight-pull strength.

6 Claims, 1 Drawing Sheet

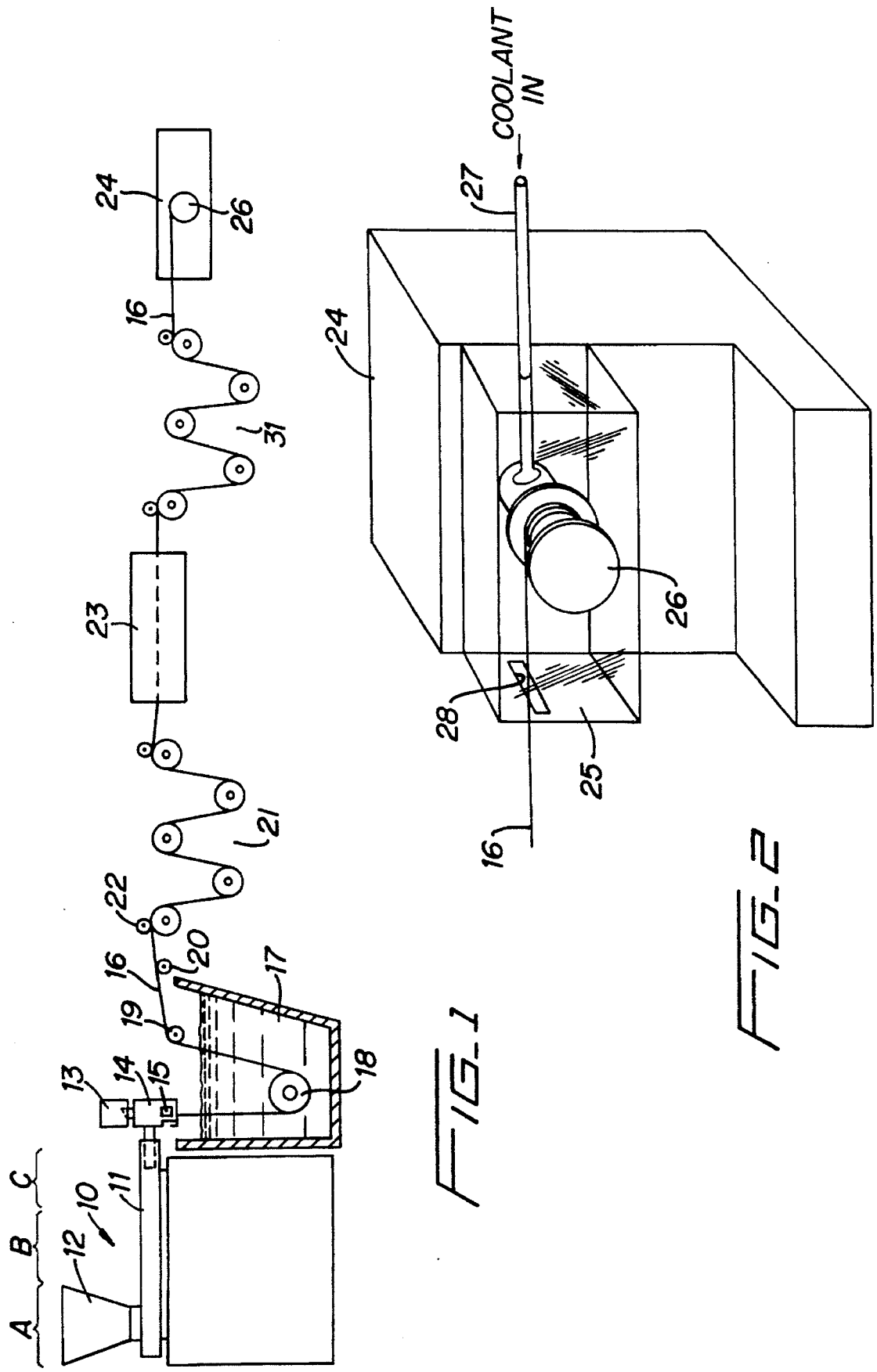

METHOD OF MANUFACTURING A MONOFILAMENT SUTURE

BACKGROUND OF THE INVENTION

This invention relates to a method of manufacturing a monofilament and to the resulting monofilament. More particularly, this invention relates to a method of manufacturing a monofilament possessing increased strength, e.g., tenacity, and improved physical characteristics such as straight-pull strength and knot-pull strength.

Methods for making monofilaments that are suitable for use as surgical sutures are known and generally include the steps of extruding at least one bioabsorbable or nonbioabsorbable polymer to provide a monofilament, quenching the monofilament to effect its solidification, drawing/stretching the solidified monofilament to achieve molecular orientation and impart high tenacity to the monofilament and annealing the drawn/stretched monofilament to relieve internal stresses. See, e.g., U.S. Pat. Nos. 3,092,891, 3,106,442, 3,630,205, 4,911,165, 5,217,485 and U.K. Patent Specification No:. 1,588,031 and European Patent Application No. 415,783.

SUMMARY OF THE INVENTION

It has been discovered that if in a monofilament manufacturing process the monofilament is exposed to temperatures ranging from about −50° to about 0° C. after being drawn or stretched the resulting monofilament will exhibit increased strength, i.e., tenacity, and improved physical properties such as straight-pull strength and knot-pull strength.

In accordance with this invention, in a continuous monofilament manufacturing process, in which a polymer is melt extruded and quenched to provide a solidified monofilament and the solidified monofilament is subjected to stretching and annealing operations to provide a monofilament suitable for use as a surgical suture, an improvement is provided which comprises exposing the stretched monofilament to low temperatures ranging from about −50° to about 0° C. for periods of time ranging from about 0.5 minutes to about 4 hours. The step of exposing the stretched monofilament to such temperatures after the stretching operation is hereinafter referred to as the "cooling" step. The monofilament which is thus exposed can be further treated (e.g., stretched or annealed in a manner known in the art) to provide a surgical suture exhibiting improved physical properties.

The monofilament of this invention can be employed in the fabrication of medical/surgical devices such as monofilament and multifilament sutures; woven, knit or braided fabric prostheses; fasteners, meshes, and the like.

BRIEF DESCRIPTION OF THE DRAWINGS

FIG. 1 is a schematic illustration of an apparatus which is suitable for carrying out the extruding, quenching, stretching and cooling steps of the monofilament manufacturing process of this invention.

FIG. 2 is a perspective view depicting a cooling unit which can be employed in the method of this invention.

DESCRIPTION OF THE PREFERRED EMBODIMENTS

In general, the conditions of the individual steps of extruding, quenching, drawing and annealing in the monofilament manufacturing process of this invention can be substantially the same as those described in U.S. Pat. No. 5,217,485, the contents of which are hereby incorporated by reference herein. Similarly, the process herein can employ much the same type apparatus as that described in U.S. Pat. No. 5,217,485.

FIG. 1 schematically illustrates a particularly useful manufacturing operation for extruding, quenching, stretching and cooling a monofilament in accordance with this invention. Extruder unit 10 is of a known or conventional type and is equipped with controls for regulating the temperature of barrel 11 in various zones thereof, e.g., progressively higher temperatures in three consecutive zones A, B and C along the length of the barrel. Pellets or powder of polymer are introduced to the extruder through drier-hopper 12. Suitable polymers include those that are bioabsorbable and nonbioabsorbable. Examples of bioabsorbable polymers which can be employed in the process of this invention include polymers, copolymers and polymeric blends derived from monomers known to provide biocompatible, bioabsorbable polymers. Such monomers include glycolide, glycolic acid, lactide, lactic acid, p-dioxanone, trimethylene carbonate, epsilon-caprolactone, and the like. Examples of nonbioabsorbable polymers which can be employed in the process of this invention include polyethylene, polypropylene, nylon, polyethylene terephthalate, and the like.

Motor-driven metering pump 13 delivers melt extruded polymer at a constant rate to spin pack 14 and thereafter through a spinneret 15 possessing one or more orifices of desired diameter to provide a molten monofilament 16 which then enters quench bath 17, e.g., containing water, where the monofilament solidifies. The distance monofilament 16 travels after emerging from spinneret 15 to the point where it enters quench bath 17, i.e., the air gap, can vary and can advantageously be from about 0.5 to about 100 cm. If desired, a chimney (not shown), or shield, can be provided to reduce the length of the air gap, e.g., from 1 to 10 cm, thereby isolating monofilament 16 from contact with air currents which might otherwise affect the cooling of the monofilament in an unpredictable manner. Monofilament 16 is passed through quench bath 17 around driven roller 18 and over idle rollers 19 and 20. Optionally, a wiper (not shown) may remove excess water from the monofilament as it is removed from quench bath 17. On exiting the quench bath the monofilament enters first godet station generally indicated at 21.

First godet station 21 is equipped with five individual godets around which monofilament 16 is wrapped. The first individual godet is equipped with nip roll 22 to prevent slippage which might otherwise result. Upon entering first godet station 21, monofilament 16 passes over the first godet, under the second godet, over the third godet, under the fourth godet and over the fifth godet. The fifth godet is likewise equipped with a nip roll.

Monofilament 16 passing from first godet station 21 is stretched to effect the molecular orientation of the polymer from which it is fabricated and thereby further increase the tensile strength of the monofilament. Stretching may be achieved by drawing the monofilament while or after it has been heated. In the stretching operation shown in FIG. 1, monofilament 16 is drawn through heating unit 23 by means of second godet station generally indicated at 31 which rotates at a higher speed than first godet station 21 to provide the desired stretch ratio. For larger size sutures, e.g., sizes 2 to 2/0, heating unit 23 may comprise a hot liquid (such as water or glycerol) bath through which monofilament 16 passes. For smaller size sutures, e.g., sizes 3/0 to 8/0, heating unit 23 may comprise a hot air convection oven chamber.

Following the stretching operation, monofilament 16 optionally can be subjected to additional stretching or an on-line annealing/relaxation (shrinkage) operation. In accordance with methods that are known and described in the art, on-line annealing with or without relaxation when desired is accomplished by driving the monofilament through a second heating unit by a third godet station (not shown). For relaxation, the third godet station rotates at a slower speed than the second godet station thus relieving tension on the monofilament.

Thereafter, monofilament 16 enters cooling unit 24 and is collected on take-up reel 26 which is located within cooling unit 24. Monofilament 16 within cooling unit 24 is exposed to temperatures ranging from about −50° to about 0° C., preferably from about −20° to about −5° C. and most preferably from about −15° to about −10° C. Liquid nitrogen or any other suitable refrigerant/coolant or method of obtaining the desired temperatures can be employed in the present invention. The use of liquid nitrogen is preferred. The monofilament can advantageously be exposed to these temperatures for a period of time ranging from about 0.5 minutes to about 4 hours, preferably from about 30 minutes to about 3 hours and most preferably from about 1 to about 2 hours.

A preferred embodiment of cooling unit 24 is depicted in FIG. 2. In FIG. 2, cooling unit 24 is equipped with rotatable take-up reel 26 which is housed within box 25. Take-up reel 26 is used to collect monofilament 16 as it travels down-line from the stretching operation and enters box 25 through window 28. Box 25 can be constructed of any suitable plastic material. FIG. 2 shows box 25 made of a transparent plastic material which enables one to view the inside of box 25. The low temperatures used to cool monofilament 16 are obtained by introducing a coolant, e.g., liquid nitrogen, via intake feed-line 27 to the area inside takeup reel 26. Thus, the interior diameter of take-up reel 26 is cooled from the inside. Window 28 not only allows monofilament 16 to enter box 25, but also allows for coolant gas to exit box 25. Monofilament 16 is exposed to temperatures within the range of from about −50° to about 0° C. for a duration ranging from about 0.5 minutes to about 4 hours. The molecular orientation and dimensional stability of the polymer molecules effected by the stretching operation are believed to be better retained by cooling the stretched monofilament, thus providing a monofilament possessing improved physical characteristics.

Following the cooling operation, monofilament 16 optionally can be subjected to additional stretching or can be stored in a freezer or be subjected to an annealing operation as a result of which the monofilament undergoes a recrystallization or a stabilization. It is also contemplated that monofilament 16 may continuously pass through cooling unit 24 rather than being wound onto a take-up reel. Where a continuous process is used, the cooling chamber may include a plurality of spools (not shown) around which monofilament 16 is wrapped anywhere from 1 to 100 or more times to maintain monofilament 16 within the cooling chamber for an extended period of 0.5 to 30 minutes or longer. The monofilament can then be directly transferred to another station and subjected to further treatment such as another drawing/stretching operation and/or an annealing operation.

Monofilaments of the present invention can be used as monofilament sutures or to form multifilament sutures. The monofilaments can also be woven, braided or knitted either alone or in combination with absorbable or nonabsorbable fibers to form multifilament sutures or fabric prostheses having use in the surgical repair of arteries, veins, ducts, esophagi, and the like.

In order that those skilled in the art may be better able to practice the present invention, the following examples are given as an illustration of the preparation and superior characteristics of the suture and process of the present invention. It should be further noted that the invention is not limited to the specific details embodied in the examples.

EXAMPLE 1

Monofilaments fabricated from a copolymer comprising 60% by weight glycolide, 14% by weight p-dioxanone and 26% by weight trimethylene carbonate (viscosity of 1.0~1.4 dl/g measured at 30° C. and at a concentration of 0.25 g/dl in HFIP) were prepared employing the apparatus of FIGS. 1 and 2. The extruding and stretching conditions were as follows:

| CONDITIONS OF MANUFACTURING MONOFILAMENT | |
|---|---|
| Process Conditions | Extrusion Operation |
| extruder screw, rpm | 1.5 |
| pump, rpm | 7 |
| driven roller, mpm | 5.6 |
| barrel temp., °C., zone A | 187 |
| barrel temp., °C., zone B | 190 |
| barrel temp., °C., zone C | 190 |
| clamp temp., °C. | 191 |
| adapter temp., °C. | 190 |
| pump temp., °C. | 189 |
| barrel melt temp., °C. | 186 |
| pump melt temp., °C. | 184 |
| spinneret melt temp., °C. | 184 |
| barrel pressure, psi | 700 |
| pump pressure, psi | 300 |
| pump size, cc per revolution | 0.297 |
| diameter of spinneret orifices, mm | 1.25 |
| no. of spinneret orifices | 1 |
| quench bath temp., °C. | 18 |
| depth of driven roller, cm | 16.5 |
| | Stretching (Orienting) Operation |
| draw oven temp., °C. | 26 |
| first godet station, mpm | 5.6 |
| second godet station, mpm | 29.6 |
| third godet station, mpm | 29.8 |
| draw ratio | 5.3:1 |
| | Cooling Operation |
| tension for the winder, g | 30 |
| cooling unit temp., °C. | −13 |
| duration of cooling, hours | about 1 |
| | Annealing Operation |
| annealing temp., °C. | 105 |
| duration of annealing, hours | 6 |

For comparative purposes, an attempt was made to produce a control monofilament fabricated from the same copolymer as in Example 1, using the same extrusion, stretching and annealing conditions presented above, however, the control sample was not subjected to the cooling operation.

The physical properties of the control sample were unobtainable because individual monofilaments fused together on take-up reel 26. The physical properties of the monofilament of Example 1 were measured on an Instron Tensile tester (Instron Corp.) using the following procedures:

| PROCEDURES FOR MEASURING PHYSICAL PROPERTIES OF MONOFILAMENTS | |
| --- | --- |
| Physical Property | Test Procedure |
| knot-pull strength, kg | U.S.P. XXI, tensile strength, sutures (881) |
| straight-pull strength, kg | ASTM D2256-88, Instron Corporation |
| elongation at break, % | ASTM D2256-88 |

The results of these tests are set forth in the following table:

TABLE I

| | Straight-Pull Strength (kpsi) | Knot-Pull Strength (kpsi) | Elongation (%) at Breaking |
| --- | --- | --- | --- |
| EXAMPLE 1 | 80.6 | 55.2 | 41 |

As can be seen from the data in Table I, the monofilament which was subjected to the cooling operation exhibited superior physical characteristics relative to the control sample.

Obviously, modifications and variations of the present invention are possible in light of the above teachings. It is therefore to be understood that changes may be made in particular embodiments of the inventions described which are within the full intended scope of the invention as defined by the claims.

What is claimed is:

1. A monofilament manufacturing process comprising the steps of melt extruding and quenching a polymer to provide a solidified monofilament, stretching the solidified monofilament to achieve molecular orientation, cooling the stretched monofilament to maintain the dimensional stability of the stretched monofilament and optionally annealing the monofilament; wherein the stretched monofilament is cooled under temperatures ranging from about −15° to about −10° C.

2. The process of claim 1 wherein the stretched monofilament is subjected to the cooling operation for a period of time ranging from about 0.5 minutes to about 4 hours.

3. The process of claim 1 wherein the stretched monofilament is subjected to the cooling operation for a period of time ranging from about 30 minutes to about 3 hours.

4. The process of claim 1 wherein the polymer comprises a bioabsorbable polymer.

5. The process of claim 4 wherein the bioabsorbable polymer comprises a homopolymer, copolymer or blend obtained from one or more monomers selected from the group consisting of glycolide, glycolic acid, lactide, lactic acid, p-dioxanone, epsilon-caprolactone and trimethylene carbonate.

6. The process of claim 1 wherein the polymer comprises a nonbioabsorbable polymer selected from the group consisting of polyethylene, polypropylene, nylon, polyethylene terephthalate, polybutylene terephthalate and polyvinylidene fluoride.

* * * * *